United States Patent [19]

Ide et al.

[11] Patent Number: 5,080,707
[45] Date of Patent: Jan. 14, 1992

[54] LIFE-PROLONGING AGENT FOR CUT FLOWER AND METHOD FOR TREATMENT OF CUT FLOWER

[75] Inventors: Hisao Ide, Kitajima; Kazuo Kamagata, Hatoyama, both of Japan

[73] Assignee: Shikoku Chemicals Corporation, Kagawa, Japan

[21] Appl. No.: 593,884

[22] Filed: Oct. 5, 1990

[30] Foreign Application Priority Data

Oct. 6, 1989 [JP] Japan .................................. 1-262731
Dec. 8, 1989 [JP] Japan .................................. 1-319323

[51] Int. Cl.$^5$ ............................................. A01N 3/02
[52] U.S. Cl. ................................................ 71/68; 47/58
[58] Field of Search .................... 544/190; 424/400; 427/4; 47/58; 71/68

[56] References Cited

U.S. PATENT DOCUMENTS

| | | | |
|---|---|---|---|
| 3,712,891 | 1/1973 | Berkowitz | 544/190 |
| 3,898,222 | 8/1975 | Hill | 544/190 |
| 3,919,217 | 10/1975 | Sawhill | 544/190 |
| 4,404,296 | 9/1983 | Schäpel | 524/308 |
| 4,594,239 | 6/1986 | Pluim | 514/805 |

*Primary Examiner*—Thurman K. Page
*Assistant Examiner*—Amy Hulina
*Attorney, Agent, or Firm*—Sherman and Shalloway

[57] ABSTRACT

A cut flower is immersed in an aqueous solution containing chloroisocyanuric acid or its salt. By this treatment, freshness of the color and gloss of the cut flower is maintained over a long period and a high life-prolonging effect is attained.

7 Claims, No Drawings

LIFE-PROLONGING AGENT FOR CUT FLOWER AND METHOD FOR TREATMENT OF CUT FLOWER

BACKGROUND OF THE INVENTION

1. Field of the Invention

The present invention relates to an agent and method for maintaining freshness in a cut flower over a long period.

2. Description of the Prior Art

It has been considered that shortening of the life of a cut flower is due to reduction of water rising by closure of a duct of a stalk caused by putrefaction of water and also due to discontinuation of supply of nutriments to the flower. As the agent for prolonging the life of a cut flower, there are known (1) a fungicide for preventing putrefaction of water, (2) a saccharide as a nutriment and (3) an agent for preventing evaporation of water from leaves.

Sodium hypochlorite has been generally used as the life-prolonging agent for a cut flower, and sucrose and phosphoric acid have been used nutriments.

As the conventional method for treating a cut flower after harvesting, there has been adopted a method using an aqueous solution containing 8-hydroxyquinoline, aluminum sulfate, STS (a mixture of silver nitrate and sodium thiosulfate) and sucrose.

As other life-prolonging agent for a cut flower, there are known an agent comprising phytic acid (see Japanese Unexamined Patent Publication No, 59-204112), an aqueous solution of hydrogen peroxide (see Japanese Unexamined Patent Publication No. 61-165301), an aqueous solution of sodium thiosulfate (see Japanese Unexamined Patent Publication No. 63-222101) and an aqueous solution containing sodium alginate (see Japanese Unexamined Patent Publication No. 61-165301).

Of the constituents of the life-prolonging agent for a cut flower, sodium hypochlorite (hereinafter referred to as "NaOCl") heretofore used as the fungicide for preventing putrefaction of water alkaline, and therefore, NaOCl is defective in that absorption of water is degraded in a short time.

According to the method for treating a cut flower after harvesting with an aqueous solution of a chemical such as STS, it is still difficult to maintain freshness, that is, fresh color or gloss, and prevent bluing in roses and the like.

Moreover, other known life-prolonging agents cannot show a satisfactory life-prolonging effect in typical cut flowers of chrysanthemum, rose, carnation and white lily.

SUMMARY OF THE INVENTION

We made research with a view to developing a treatment method for exerting a life-prolonging effect in a cut flower of carnation, rose or chrysanthemum and preventing reduction of color and gloss of the cut flower, such as bluing, and as the result, we found that if a cut flower is immersed in an aqueous solution containing chloroisocyanuric acid or a salt thereof, the life of the flower is prolonged and freshness of the flower is maintained over a long period. We have now completed the present invention based on this finding.

More specifically, in accordance with one aspect of the present invention, there is provided a life-prolonging agent for a cut flower, which comprises chloroisocyanuric acid or a salt thereof as an effective component.

In accordance with another aspect of the present invention, there is provided a method for treating a cut flower, which comprises immersing a stalk of a cut flower in an aqueous solution containing chloroisocyanuric acid or a salt thereof.

DETAILED DESCRIPTION OF THE INVENTION

As typical instances of the chloroisocyanuric acid and salt thereof, there can be mentioned trichloroisocyanuric acid (hereinafter referred to as "TCIA"), dichloroisocyanuric acid, sodium dichloroisocyanurate (hereinafter referred to as "SDIC"), potassium dichloroisocyanurate (hereinafter referred to as "PDIC") and sodium dichloroisocyanurate dihydrate (hereinafter referred to as "DICD"). Among them, SDIC, PDIC and DICD having a high solubility are preferably used.

As the saccharide used for the life-prolonging agent of the present invention, there can be mentioned glucose, mannose, galactose, maltose and sucrose, and the saccharide is added to the aqueous solution at a concentration of about 0.5 to about 5.0% by weight.

As the acid and salt used in the present invention, there can be mentioned organic acids such as succinic acid, adipic acid, citric acid and ascorbic acid, and inorganic salts such as sulfates, nitrates and phosphates. The acid or salt is incorporated into the aqueous solution at a concentration of about $1 \times 10^{-4}$ to about $5 \times 10^{-4}$ mole/l.

The life-prolonging agent of the present invention can be handled in the form of a powder, a granule, an easily soluble foamed tablet or an aqueous solution.

In carrying out the method of the present invention, the life-prolonging agent is used in the form of an aqueous solution having an available chlorine content of 10 to 30,000 ppm and a pH value of 3 through 7.

If the pH value of the aqueous solution exceeds the above-mentioned range, the fungicidal effect is weakened and the water-absorbing property of the cut flower is reduced. If the pH value of the aqueous solution is below the above-mentioned range, troubles are often caused.

In the case where a harvested cut flower is treated in carrying out the method of the present invention, the cut flower should be immersed in an aqueous solution containing chloroisocyanuric acid or a salt thereof at an available chlorine content of 10 to 30,000 ppm, preferably 50 to 2,000 ppm, for 10 minutes to 48 hours and be then taken out from the aqueous solution.

At this treatment, it is preferred that the available chlorine content in the treating solution should be changed appropriately according to the kind of the cut flower, the degree of contamination and the treatment time. If the treatment time is too short, no satisfactory life-prolonging effect can be obtained, and if the available chlorine content is too high, the water-absorbing property of the cut flower is reduced and troubles are caused in the cut flower.

In carrying out the method of the present invention, in the case where a cut flower is admired, the life-prolonging agent of the present invention is dissolved in water in a vessel such as a flower vase at an available chlorine content of 10 to 300 ppm, and the cut flower is continuously arranged in the vase.

In order to improve the permeability of the treating solution, a surface active agent or a plant growth-adjusting agent can be added to the treating solution according to need.

It is known that in general, if the pH value is adjusted to an acidic level, absorption of water by a cut flower is promoted and propagation of microorganisms is inhibited. Since chloroisocyanuric acid or a salt thereof used in the present invention can maintain an acidic state in the aqueous solution stably, putrefaction of water can be prevented over a long period and the phenomenon of closure of a duct of a cut flower is not caused.

In the method of the present invention, when a cut flower is immersed in an aqueous solution of chloroisocyanuric acid or a salt thereof, generation of ethylene, which is a growth hormone generated in a plant, can be controlled, and therefore, freshness of the flower can be maintained over a long period.

The present invention will now be described in detail with reference to the following examples that by no means limit the scope of the invention.

EXAMPLE 1

SDIC was dissolved in distilled water to form an aqueous solution having an available chlorine content adjusted to 10 to 600 ppm, and chrysanthemum (the weight of one stalk was 20 to 25 g) just after harvesting was immersed in the aqueous solution, and the cut flower was maintained at room temperature (25° to 32° C.) and the state of the flower was examined with the lapse of time. After 13 days, the amount of water absorbed by the chrysanthemum and the pH value of the aqueous solution were measured. The state of occurrence of troubles was judged by the visual observation and the life of the flower was evaluated. The obtained test results are shown in Table 1.

Incidentally, in Table 1 and subsequent tables, the amount of absorbed water indicates the amount of water absorbed during the test period per gram of the cut flower.

TABLE 1

| Available Chlorine Content (ppm) | pH | Amount (g) of Absorbed Water | Life (days) |
|---|---|---|---|
| 0 | 7.3 | 2.87 | 7 |
| 10 | 6.2 | 3.87 | 9 |
| 50 | 5.5 | 4.31 | 12 |
| 100 | 4.6 | 4.31 | 12 |
| 200 | 4.1 | 4.31 | 12 |
| 400 | 3.3 | 2.30 | 7 |
| 600 | 2.9 | 2.58 | 5 |

From the above test results, it was confirmed that the amount of water absorbed by chrysanthemum in case of the aqueous solution containing SDIC was larger than in case of the aqueous solution free of SDIC, and the life of the flower was prolonged by SDIC.

However, if the available chlorine content became too high, the amount of water absorbed by the flower was decreased, and the life was shortened and troubles appeared on leaves. When the test was similarly carried out by using PDIC or DICD instead of SDIC, the obtained results were substantially the same as those obtained in case of SDIC.

EXAMPLE 2

The test was carried out in the same manner as described in Example 1 except that TCIA was used instead of SDIC. The obtained results are shown in Table 2.

TABLE 2

| Available Chlorine Content (ppm) | pH | Amount (g) of Absorbed Water | Life (days) |
|---|---|---|---|
| 0 | 7.3 | 2.87 | 7 |
| 10 | 5.4 | 4.01 | 9 |
| 50 | 4.9 | 5.11 | 12 |
| 100 | 4.4 | 4.92 | 11 |
| 200 | 3.3 | 4.91 | 10 |
| 400 | 2.7 | 3.30 | 5 |
| 600 | 2.1 | 2.62 | 3 |

From the above test results, it was found that the amount of water absorbed by the flower and the life of the flower were substantially the same as those obtained in Example 1 where SDIC was used.

EXAMPLE 3

The test was carried out in the same manner as described in Example 1 except that white lily was used. The obtained results are shown in Table 3.

TABLE 3

| Available Chlorine Content (ppm) | pH | Amount (g) of Absorbed Water | Life (days) |
|---|---|---|---|
| 0 | 7.3 | 1.97 | 5 |
| 10 | 5.4 | 2.07 | 8 |
| 50 | 4.6 | 2.27 | 9 |
| 100 | 4.3 | 2.36 | 8 |
| 200 | 3.9 | 2.36 | 8 |
| 400 | 3.7 | 2.30 | 5 |
| 600 | 3.3 | 1.95 | 5 |

From the above results, it was confirmed that a life-prolonging effect was attained also in case of white lily as in case of chrysanthemum.

EXAMPLE 4

The test was carried out in the same manner as described in Example 3 except that $1 \times 10^{-4}$ mole/l of an organic acid or an inorganic acid and 1% by weight of a saccharide were added to the aqueous solution of SDIC and the initial chlorine available chlorine content was adjusted to 100 ppm. The obtained results are shown in Table 4.

TABLE 4

| Composition | pH | Life (days) | Amount (g) of Absorbed Water |
|---|---|---|---|
| SDIC | 4.5 | 10 | 2.47 |
| SDIC + succinic acid | 4.3 | 12 | 2.09 |
| SDIC + citric acid | 4.3 | 12 | 1.94 |
| SDIC + $Al_2(SO_4)_3$ | 4.2 | 13 | 1.97 |
| SDIC + $MgSO_4$ | 4.3 | 13 | 1.99 |
| SDIC + fructose | 4.2 | 12 | 2.15 |
| SDIC + sucrose | 4.4 | 13 | 2.81 |
| SDIC + sucrose + adipic acid | 4.1 | 12 | 2.82 |
| SDIC + sucrose + $AL_2(SO_4)_3$ | 4.0 | 12 | 2.94 |

EXAMPLE 5

The test was carried out by using cut flowers of rose in the same manner as in Example 3 (the initial available chlorine content of SDIC was 100 ppm). The obtained results are shown in Table 5.

In the present example, the life of the flower was determined according to the following formula:

$$\text{life (days)} = \frac{\Sigma\, ni \times di}{N}$$

wherein ni represents the number of flowers which have arrived at the terminal point, di represents the number of days to the terminal point, and N represents the number of flowers tested (N is 3 in the present example).

TABLE 5

| Composition | pH | Life (days) | Amount (g) of Absorbed Water |
|---|---|---|---|
| SDIC | 5.5 | 4.3 | 1.44 |
| SDIC + 0.5% sucrose | 5.1 | 4.7 | 2.69 |
| SDIC + 1.0% sucrose | 5.1 | 6.3 | 3.33 |
| SDIC + 3.0% sucrose | 4.8 | 8.2 | 3.78 |
| SDIC + 1.0% sucrose + $Al_2(SO_4)_3$ | 4.3 | 6.8 | 3.94 |
| SDIC + 1.0% sucrose + L-ascorbic acid | 4.1 | 6.8 | 3.44 |

EXAMPLES 6 AND 7 AND COMPARATIVE EXAMPLES 1 THROUGH 6

Aqueous solutions having an available chlorine content shown in Table 6 were prepared by using SDIC, sodium hypochlorite or calcium hypochlorite, and sucrose was added to each solution at a concentration of 3% to form 2 l of a test solution. Ten stalks of chrysanthemum just after harvesting were immersed in the test solution for a predetermined time shown in Table 6. Then, the stalks were taken out from the aqueous solution. Then, the cut flowers were transferred into a vessel charged with city water and placed in a room maintained at 26° to 30° C. After the lapse of the predetermined number of days, the number of healthy flowers, the pH value of the aqueous solution, and the ratio of the diameter of the flower at the time when the diameter of the flower was largest during the test period to the largest diameter of the untreated flower were determined. Incidentally, city water was replaced by fresh city water once every two days.

The obtained results are shown in Table 7.

TABLE 6

| | Test Solution | Available Chlorine Content (ppm) | pH | Immersion time (hours) |
|---|---|---|---|---|
| Example 5 | SDIC | 200 | 6.1 | 24 |
| Example 6 | SDIC | 1,000 | 5.5 | 2 |
| Comparative Example 1 | NaOCl | 200 | 8.8 | 24 |
| Comparative Example 2 | NaOCl | 1,000 | 9.6 | 2 |
| Comparative Example 3 | calcium hypochlorite | 200 | 9.7 | 24 |
| Comparative Example 4 | calcium hypochlorite | 1,000 | 10.8 | 2 |
| Comparative Example 5 | STS | — | 6.7 | 24 |
| Comparative Example 6 | blank | — | 7.2 | — |

TABLE 7

| | Number of Healthy Flowers | | | Flower Diameter Increase Ratio (%) |
|---|---|---|---|---|
| | after 7 days | after 10 days | after 16 days | |
| Example 6 | 10 | 10 | 9 | 155 |
| Example 7 | 10 | 9 | 9 | 152 |
| Comparative Example 1 | 9 | 7 | 6 | 122 |

TABLE 7-continued

| | Number of Healthy Flowers | | | Flower Diameter Increase Ratio (%) |
|---|---|---|---|---|
| | after 7 days | after 10 days | after 16 days | |
| Comparative Example 2 | 9 | 7 | 5 | 115 |
| Comparative Example 3 | 9 | 7 | 5 | 117 |
| Comparative Example 4 | 8 | 6 | 5 | 112 |
| Comparative Example 5 | 6 | 5 | 4 | 103 |
| Comparative Example 6 | 6 | 4 | 2 | 100 |

EXAMPLES 8 THROUGH 14

An aqueous solution of SDIC or TCIA having an available chlorine content of 200 ppm was prepared, and sucrose, burnt alum, succinic acid, sodium citrate and sodium dihydrogenphosphate were added in amounts shown in Table 8 to the aqueous solution to form 2 l of a test solution.

TABLE 8

| Example No. | Composition | pH |
|---|---|---|
| 8 | SDIC + sucrose (1%) | 4.1 |
| 9 | TCIA + sucrose (3%) | 3.3 |
| 10 | SDIC + sucrose (3%) | 3.8 |
| 11 | SDIC + sucrose + burnt alum (3%) (100 ppm) | 3.9 |
| 12 | SDIC + sucrose + succinic acid (3%) (100 ppm) | 3.9 |
| 13 | SDIC + sucrose + sodium citrate (3%) (100 ppm) | 4.2 |
| 14 | SDIC + sucrose + sodium dihydrogen-(3%) phosphate (100 ppm) | 4.8 |

Ten stalks each of three varieties of rose (Marina, Super Star and Sonia) were immersed for 24 hours in three conical beakers charged with the above test solution, respectively.

The three conical beakers were placed in a room maintained at 20° to 25° C., and the number of days which had elapsed until the flowers became unfit for admiration or troubles were caused in the flowers was determined. The determined number of days was divided by the number of the flowers, and the obtained value was designated as the flower life day number. For comparison, the flower life day numbers of rose treated with a solution of STS and untreated rose were similarly determined.

The obtained results are shown in Table 9.

TABLE 9

| | Flower Life Day Number (days) | | |
|---|---|---|---|
| Test Solution | Marina | Super Star | Sonia |
| Example 8 | 9.7 | 7.8 | 10.7 |
| Example 9 | 12.0 | 8.2 | 12.3 |
| Example 10 | 11.8 | 8.7 | 13.3 |
| Example 11 | 14.3 | 11.9 | 15.7 |
| Example 12 | 13.5 | 11.9 | 15.3 |
| Example 13 | 12.5 | 10.6 | 14.0 |
| Example 14 | 12.3 | 10.1 | 15.5 |
| STS | 8.7 | 7.3 | 10.5 |
| city water | 8.3 | 7.2 | 9.2 |

In the rose treated according to the method of the present embodiment, any of color changes such as bluing was not observed at all.

As is apparent from the foregoing description, if a cut flower is treated with the life-prolonging agent of the present invention, freshness of the color and gloss of the flower can be maintained over a long period.

We claim:

1. A method for treating a cut flower, which comprises immersing a stalk of a cut flower in an aqueous solution containing chloroisocyanuric acid or a salt thereof.

2. A method for treating a cut flower, which comprises immersing a stalk of a harvested cut flower in an aqueous solution of chloroisocyanuric acid or a salt thereof having an available chlorine content adjusted to 10 to 30,000 ppm and having a pH value of from 3-7 for from about 10 minutes to about 48 hours and then withdrawing the cut flower from the aqueous solution.

3. A method for treating a cut flower, which comprises continuously immersing a stalk of a cut flower in an aqueous solution of chloroisocyanuric acid or a salt thereof having an available chlorine content adjusted to 10 to 300 ppm and having a pH value of from 3-7.

4. A method for treating a cut flower according to claim 3, wherein said aqueous solution contains from about 0.5 to about 5% by weight of saccharide.

5. A method for treating a cut flower according to claim 3, wherein said aqueous solution further comprises from about $1 \times 10^{-4}$ to about $5 \times 10^{-4}$ mole/l of aluminum sulfate.

6. A method for treating a cut flower according to claim 3, wherein said aqueous solution further comprises from about 0.5 to about 5% by weight of saccharide and from about $1 \times 10^{-4}$ to about $5 \times 10^{-4}$ mole/l of aluminum sulfate.

7. A method for treating a cut flower according to claim 3, wherein said aqueous solution additionally comprises a surface active agent or plant growth-adjusting agent.

* * * * *